(12) United States Patent
Lifshitz-Liron et al.

(10) Patent No.: US 7,368,606 B2
(45) Date of Patent: May 6, 2008

(54) AMORPHOUS CINACALCET HYDROCHLORIDE AND PREPARATION THEREOF

(75) Inventors: Revital Lifshitz-Liron, Hertzlia (IL); Michael Pinchasov, Rishon-Lezion (IL); Shlomit Wizel, Petah Tiqva (IL); Sharon Avhar-Maydan, Givataym (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/439,705

(22) Filed: May 23, 2006

(65) Prior Publication Data

US 2007/0054963 A1   Mar. 8, 2007

Related U.S. Application Data

(60) Provisional application No. 60/750,910, filed on Dec. 15, 2005, provisional application No. 60/742,626, filed on Dec. 5, 2005, provisional application No. 60/739,215, filed on Nov. 22, 2005, provisional application No. 60/738,827, filed on Nov. 21, 2005, provisional application No. 60/734,669, filed on Nov. 7, 2005, provisional application No. 60/702,918, filed on Jul. 26, 2005, provisional application No. 60/698,613, filed on Jul. 11, 2005, provisional application No. 60/684,152, filed on May 23, 2005.

(51) Int. Cl.
*C07C 211/00* (2006.01)
(52) U.S. Cl. .................................................. 564/337
(58) Field of Classification Search ................ 564/337
See application file for complete search history.

(56) References Cited

U.S. PATENT DOCUMENTS

| | | | |
|---|---|---|---|
| 4,966,988 A | 10/1990 | Schinski et al. | |
| 5,648,541 A | 7/1997 | Van Wagenen et al. | |
| 6,011,068 A | 1/2000 | Nemeth et al. | |
| 6,031,003 A | 2/2000 | Nemeth et al. | |
| 6,211,244 B1 | 4/2001 | Van Wagenen et al. | |
| 6,313,146 B1 | 11/2001 | Van Wagenen et al. | |
| 2005/0147669 A1 | 7/2005 | Lawrence et al. | |
| 2005/0234261 A1 | 10/2005 | Wilken et al. | |
| 2006/0276534 A1* | 12/2006 | Martin et al. ................ | 514/464 |

FOREIGN PATENT DOCUMENTS

WO   WO 2006/125026   11/2006

OTHER PUBLICATIONS

"Sensipar (Cinacalcet HCl) Tablets" Summary Basis of Approval of New Drug Application #21-688 By FDA, (2004).
J. Iqbal, et al. "Cinacalcet Hydrochloride" *IDrugs*, vol. 6, No. 6, p. 587-592, (2003).
L.A. Sorbers, et al. "Cinacalet Hydrochloride" *Drugs of the Future*, vol. 27, No. 9, p. 831-836, (2002).
X. Wang, et al. "Synthesis of Cinacalcet Congeners" *Tetrahedron Letters*, vol. 45, p. 8355-8358, (2004).
Snyder, L.R. et al., *Introduction To Modern Liquid Chromatography*, 2nd Ed., (1979), pp. 549-572, John Wiley & Sons, Inc.
Strobel, H.A. et al., *Chemical Instrumentation: A Systematic Approach*, 3rd Ed., (1989), pp. 391-393, 879-894, 922-925, 953.
Devasher et al., "Aqueous-Phase, Palladium-catalyzed cross-coupling of aryl bromides under mild conditions, using water soluable, sterically demanding alkylphosphines", Journal of Organic Chemistry, American Chemical Society, vol. 69, 2004, pp. 7919-7927.
Database Belistein; Belistein Institute for Organic Chemistry, Frankfurt-Main, DE; XP002451055 (& Pharmazie, vol. 59, No. 10, 2004, pp. 744-752).
Anonymous, "N-[1-(R)-(–)-(1-naphthyl)]-3-[3-[3-(trifluoromethyl)phenyl]-1-aminopropane hydrochloride", IP.COM Journal, May 23, 2005, XPO002424259.

* cited by examiner

*Primary Examiner*—Samuel A Barts
(74) *Attorney, Agent, or Firm*—Kenyon & Kenyon LLP

(57) ABSTRACT

Provided is amorphous cinacalcet hydrochloride, processes for the preparation thereof, and pharmaceutical compositions therewith.

26 Claims, 4 Drawing Sheets

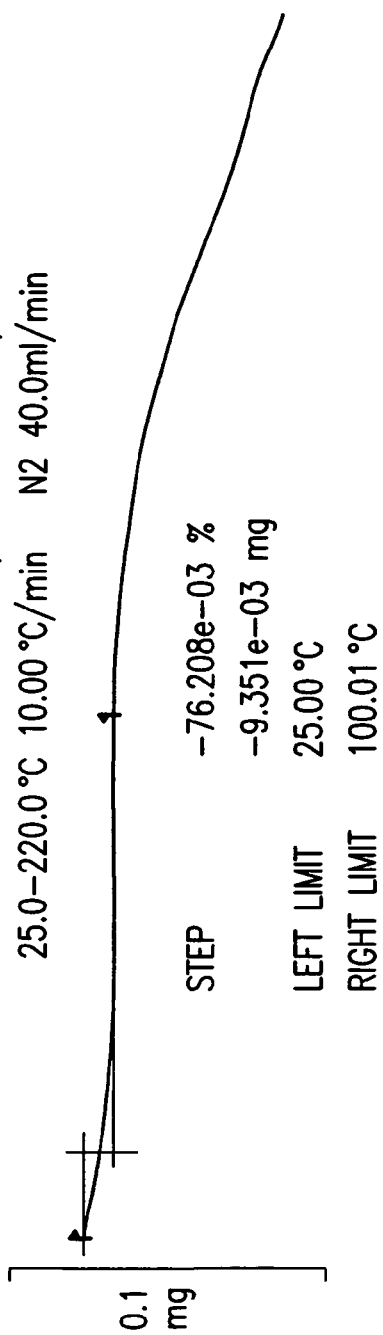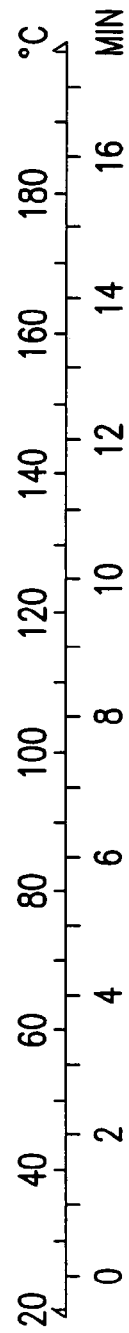
FIG.4

AMORPHOUS CINACALCET HYDROCHLORIDE AND PREPARATION THEREOF

CROSS-REFERENCE TO RELATED APPLICATIONS

This application claims the benefit of U.S. Provisional Applications Nos. 60/684,152, filed May 23, 2005; 60/698,613, filed Jul. 11, 2005; 60/702,918, filed Jul. 26, 2005; 60/734,669, filed Nov. 7, 2005; 60/738,827, filed Nov. 21, 2005; 60/750,910, filed Dec. 15, 2005; 60/739,215, filed Nov. 22, 2005; and 60/742,626, filed Dec. 5, 2005, hereby incorporated by reference.

FIELD OF THE INVENTION

The present invention relates to amorphous cinacalcet hydrochloride, processes for preparation thereof, and stable pharmaceutical compositions therewith.

BACKGROUND OF THE INVENTION (R)-α-methyl-N-[3-[3-(trifluoromethyl)phenyl]propyl]-1-naphthalenemethane amine (herein "Cinacalcet" or "CNC") has a CAS number of 226256-56-0, a formula of $C_{22}H_{22}F_3N$ and the following structure:

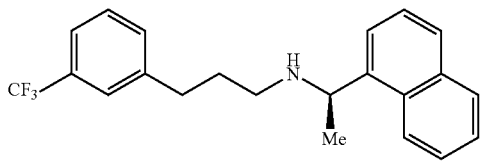

Cinacalcet is the free base form of Cinacalcet hydrochloride (herein "CNC-HCl" or "cinacalcet HCl"), which has a CAS number of 364782-34-3 and the following structure:

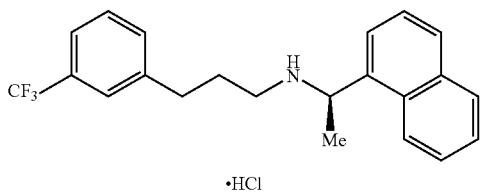

CNC-HCl is marketed as SENSIPAR™, and was the first drug in a class of compounds known as calcimimetics to be approved by the FDA. Calcimimetics are a class of orally active, small molecules that decrease the secretion of parathyroid hormone ("PTH") by activating calcium receptors. The secretion of PTH is normally regulated by the calcium-sensing receptor. Calcimimetic agents increase the sensitivity of this receptor to calcium, which inhibits the release of parathyroid hormone, and lowers PTH levels within a few hours. Calcimimetics are used to treat hyperparathyroidism, a condition characterized by the over-secretion of PTH that results when calcium receptors on parathyroid glands fail to respond properly to calcium in the bloodstream. Elevated levels of PTH, an indicator of secondary hyperparathyroidism, are associated with altered metabolism of calcium and phosphorus, bone pain, fractures, and an increased risk for cardiovascular death. As a calcimimetic, CNC-HCl is approved for treatment of secondary hyperparathyroidism in patients with chronic kidney disease on dialysis. Treatment with CNC-HCl lowers serum levels of PTH as well as the calcium/phosphorus ion product, a measure of the amount of calcium and phosphorus in the blood.

U.S. Pat. No. 6,011,068 discloses inorganic ion receptor activity, especially calcium receptor-active molecules, such as those having the general structure of cinacalcet. U.S. Pat. No. 6,211,244 discloses calcium receptor-active compounds related to cinacalcet and methods of making such compounds. Cinacalcet and its enantiomer may be produced by various methods, using the processes disclosed in U.S. Pat. No. 6,211,244; DRUGS OF THE FUTURE, 27 (9), 831 (2002); U.S. Pat. Nos. 5,648,541, 4,966,988; and Tetrahedron Letters (2004) 45: 8355, footnote 12.

The discovery of new amorphous forms of active pharmaceutical ingredients ("APIs") provides opportunities to improve the performance characteristics of a pharmaceutical product. Such discoveries enlarge the repertoire of materials that a formulation scientist has available for designing, for example, a pharmaceutical dosage form of a drug with a targeted release profile or other desired characteristic.

Generally, amorphous solids offer opportunities for solubility and bioavailability enhancement since these materials are more soluble than the crystalline form of the same compound. The rate of dissolution is also a consideration in formulating syrups, elixirs and other liquid medicaments.

None of the prior art references discussed above disclose amorphous form of Cinacalcet hydrochloride.

SUMMARY OF THE INVENTION

The invention is directed to amorphous cinacalcet hydrochloride. Preferably, the amorphous Cinacalcet hydrochloride is characterized by an X-ray diffraction pattern, substantially as depicted in FIG. 2.

The amorphous Cinacalcet HCl of the invention is preferably prepared in a process, comprising dissolving Cinacalcet HCl in chloroform; admixing an anti-solvent selected from the group consisting of aliphatic and cyclic hydrocarbons to obtain a precipitate; and drying precipitated Cinacalcet hydrochloride under reduced pressure at temperature greater than 25° C., more preferably, from about 40° C. to 60° C., and, most preferably, about 50° C. The precipitated Cinacalcet hydrochloride is preferably dried for about 16 to 30 hours. Preferably, in the process, the amorphous Cinacalcet HCl is in a concentration of about 5 to about 10 ml of chloroform per gram of Cinacalcet hydrochloride. The anti-solvent is preferably n-pentane, n-hexane, n-heptane, or cyclohexane. Subsequent to admixing the anti-solvent, the precipitate is preferably maintained as a slurry for about 5 minutes to about 20 hours.

The amorphous Cinacalcet hydrochloride of the invention is also preferably prepared in a process, comprising providing a solution of Cinacalcet hydrochloride in a solvent selected from the group consisting of a $C_2$ to $C_8$ ether, a $C_{5-8}$ cyclic, branched and/or halogenated hydrocarbon, a $C_{3-7}$ ester, a $C_{1-4}$ alcohols, a $C_{3-6}$ ketone, and mixtures thereof, and evaporating and removing the solvent by spray drying with nitrogen gas, having an inlet temperature of about 50° C. to 200° C. The solvent is preferably selected from the group consisting of ethanol, THF, 1,4-Dioxane, dichloromethane, chloroform, ethylacetate, isobutyl acetate, acetone, MEK, and acetonitrile, and is more preferably ethanol. The Cinacalcet hydrochloride is preferably at a concentration of about 5 to about 10 ml of solvent per gram of Cinacalcet hydrochloride. The evaporated solvent and nitrogen preferably exit the spray dryer at a temperature of about 25° C. to about 150° C.

The amorphous Cinacalcet hydrochloride of the invention is also preferably prepared in a process comprising providing a solution of Cinacalcet hydrochloride in a solvent, and removing the solvent by rapid vacuum evaporation under a pressure of less than about 760 mm Hg and a temperature of less than about 100° C. The pressure is preferably less than about 100 mm Hg, and, more preferably, less than about 70 mm Hg. The temperature is preferably about 20° C. to about 80° C., and, more preferably, about 25° C. to about 45° C. Preferably, the concentration and solvent of the solution, and the temperature, vacuum and feeding rate of the rapid vacuum evaporation are such that the Cinacalcet hydrochloride precipitates substantially instantly.

Useful solvents include, but are not limited to, $C_{1-4}$ alcohols, $C_{3-7}$ ketones $C_{3-7}$ ester, $C_{5-7}$ linear, branched or cyclic, saturated or unsaturated hydrocarbons, $C_2$ to $C_8$ ethers, or mixtures thereof. Preferably, the solvent is selected from the group consisting of methanol, ethanol, acetone, ethylacetate, heptane, hexane, diethylether methyl isobutylether, or mixtures thereof, and, more preferably, is methanol or acetone. Preferably, the solvent contains less than about 20% water by volume, more preferably, less than about 10% water by volume, and, most preferably, less than about 2% water by volume.

BRIEF DESCRIPTION OF THE DRAWINGS

FIG. 4 illustrates a TGA thermogram of Cinacalcet HCl Form I.

DETAILED DESCRIPTION OF THE INVENTION

As used herein, "ambient temperature" refers to a room temperature, usually at a temperature of about 18 to about 25° C., preferably about 20 to about 22° C.

Figure 1:
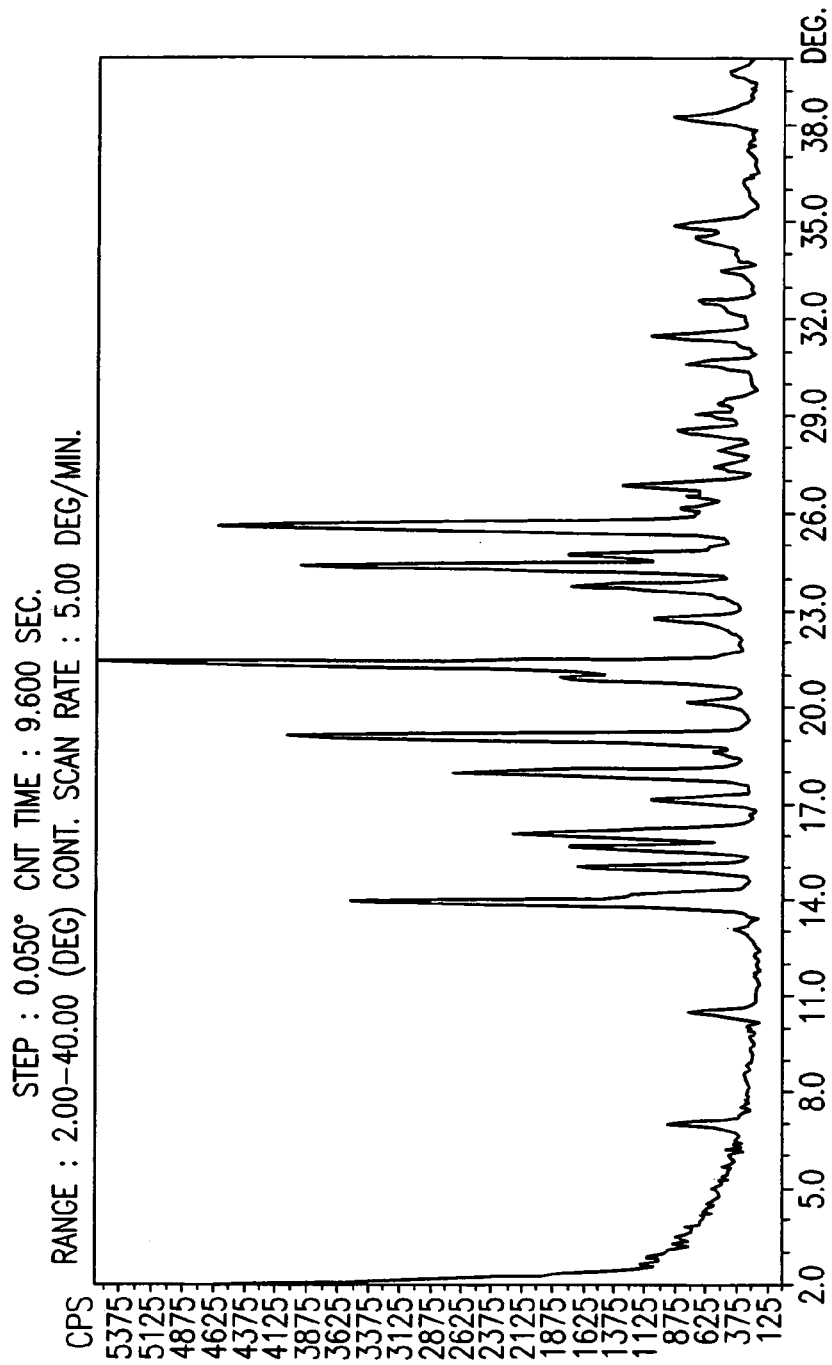
FIG. 1 illustrates an X-Ray Powder Diffraction pattern of Cinacalcet HCl Form I.
Figure 3:
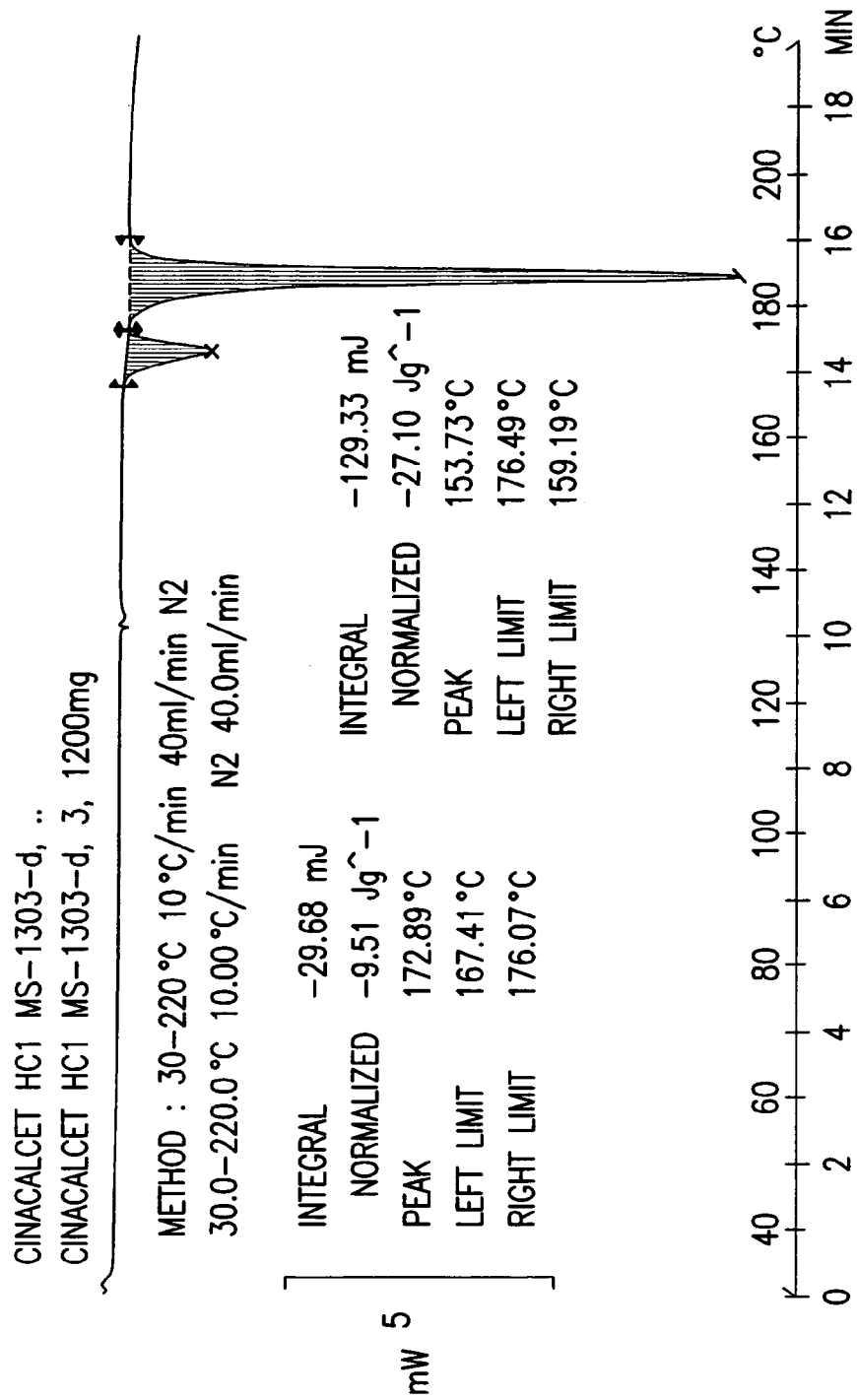
FIG. 3 illustrates a DSC thermogram of Cinacalcet HCl Form I.

In the published Summary Basis for Approval of New Drug Application #21688, it is mentioned that cinacalcet hydrochloride has only one stable crystalline form at ambient temperature. This form is designated herein as Form I and is characterized by a powder X-ray diffraction ("PXRD") peaks at about 13.9°, 19.0°, 21.3°, and 25.5°2θ±0.2°2θ. This crystalline form may be further characterized by a PXRD pattern with peaks at about 15.0°, 15.5°, 16.0°, 17.9°, 23.7°, and 24.3°2θ±0.2°2θ or substantially as depicted in FIG. 1. This crystalline form may be further characterized by a differential scanning calorimetry ("DSC") thermogram, which shows two endothermic peaks at about 160° C. to about 170° C. and at about 175° C. to about 185° C., substantially as depicted in FIG. 3. This crystalline form may be further characterized by a thermogravimetric analysis ("TGA") thermogram, substantially as depicted in FIG. 4, showing weight loss of less than 1 percent. This form may be considered anhydrous.

The cinacalcet base used to prepare the amorphous form described may be prepared according to any method known in the art such as the processes described in a co-pending U.S. Application No. 60/750,910.

Figure 2:
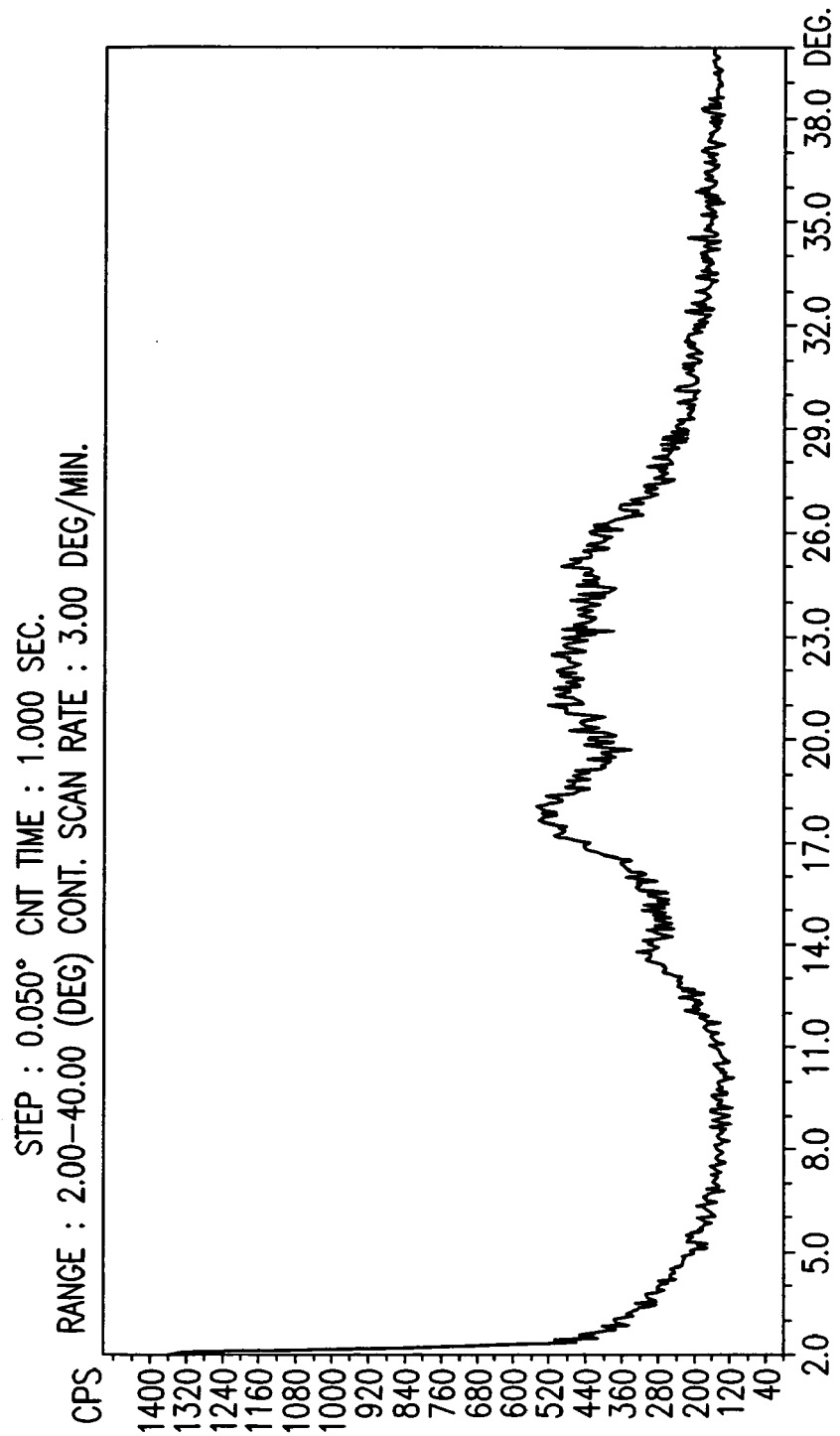
FIG. 2 illustrates an X-Ray Powder Diffraction pattern of Amorphous Cinacalcet HCl.

In one embodiment, the invention encompasses amorphous cinacalcet. Amorphous cinacalcet is characterized by a PXRD pattern, substantially as depicted in FIG. 2. This amorphous form is stable under prolonged storage, in normal conditions, as shown in Example 1. In addition, the amorphous form is stable at high humidity levels (100 percent relative humidity ("RH")), and is non-hygroscopic, as shown in Example 2.

In another embodiment, the present invention encompasses a process for preparing amorphous cinacalcet HCl comprising (a) dissolving cinacalcet HCl in chloroform, (b) admixing an anti-solvent selected from the group consisting of aliphatic and cyclic hydrocarbons to obtain a precipitate; and (c) drying the precipitated cinacalcet hydrochloride under reduced pressure at an increased temperature.

Preferably, the cinacalcet HCl is dissolved in chloroform in a concentration of about 5 to about 10 ml of chloroform per gram of cinacalcet hydrochloride, more preferably in a concentration of about 5 to 8 ml of chloroform per gram of cinacalcet hydrochloride.

Subsequent to admixing of the anti-solvent, a precipitate is preferably obtained by maintaining the slurry for about 5 minutes to about 20 hours.

Preferably, the anti-solvent is selected from the group consisting of n-pentane, n-hexane, n-heptane, and cyclohexane.

Preferably, as used herein, the term "increased temperature" refers to a temperature greater than room temperature, i.e., greater than about 25° C., more preferably, from about 40° C. to 60° C., and, most preferably, about 50° C. Preferably, drying is for about 16 to 30 hours.

In another embodiment, the present invention encompasses a process for preparing amorphous cinacalcet HCl by spray drying. Preferably, Cinacalcet HCl is dissolved in a solvent selected from the group consisting of cyclic ethers, toluene, chlorinated hydrocarbons, esters, $C_1$-$C_4$ alcohols, and ketones. Preferred cyclic ethers include tetrahydrofuran ("THF") and 1,4,-dioxane, preferred chlorinated hydrocarbons include dichloromethane and chloroform, preferred esters include ethyl acetate and isobutyl acetate, and preferred ketones include acetone, methyl ethyl ketone ("MEK"), and acetonitrile. Preferably, the nitrogen gas of the spray dryer is at an inlet temperature of about 50° C. to 200° C. In a particularly preferred embodiment, cinacalcet HCl Form I is dissolved in ethanol while the nitrogen gas of the spray dryer is at an inlet temperature of about 100° C. Amorphous cinacalcet HCl is obtained.

In another embodiment, the present invention encompasses a process for preparing amorphous cinacalcet HCl by rapid vacuum evaporation wherein an API is dried fast. The rate of flow of the solution may be in the range of about 10 to about 50 cm³/hour/nozzle, depending on the concentration, pressure, temperature, and properties of the API:solvent.

While other drying techniques may be suitable on a laboratory scale, such as for batches less than about 100 g, fast injection using the rapid vacuum allows for preparation of amorphous cinacalcet HCl on an industrial scale, i.e., a batch of at least about 500 g, more preferably at least about one kilogram, and most preferably at least about ten kilograms.

In principle, the rapid vacuum evaporation technique is applicable both for aqueous and organic solvents. However, it is preferable to use this technique with organic solvents, since organic solvents are generally more volatile than aqueous solvents. Preferred solvents are easily volatile organic solvents with relatively low boiling point such as a $C_1$ to $C_4$ alcohol, a $C_3$ to $C_7$ ketone, a $C_3$ to $C_7$ ester, a $C_5$ to $C_7$ straight or cyclic saturated hydrocarbon, a $C_2$ to $C_8$ ether, or mixtures thereof. Particularly preferred solvents may be selected from methanol, ethanol, acetone, ethyl acetate, heptane, hexane, diethyl ether methyl isobutyl ether, or mixtures thereof. Especially preferred solvents are methanol or acetone. Preferably, these solvents are used in technical grade, which contains less than about 20 percent water, more preferably less than about 10 percent water and most preferably, 2 percent water by volume. The boiling point of the solvent is preferably below about 100° C., more preferably below about 70° C., under atmospheric pressure at ambient temperature.

The starting material cinacalcet HCl is preferably at a concentration of about 20 to about 80 m/m percent, more preferably about 60-75 percent, and is introduced into a reduced pressure chamber at elevated temperature through a syringe or preferably a nozzle. The feeding may be carried out by a pump, pressure from another tank or vacuum in the drying chamber. When the solution reaches the drying chamber, the solvent evaporates substantially instantly, while the dissolved cinacalcet HCl precipitates as a scum (solid foam) or sometimes as a solid. The scum grows due to continuous feeding, hanging on the syringes/nozzles. When the scum reaches a certain mass, it falls down to the bottom of the drying chamber.

The concentration, solvent type, temperature, vacuum, and feeding rate are set so that cinacalcet HCl, coming from the syringe, precipitates instantly. The number of inlets for the nozzles in the drying chamber depends on the capacity of vacuum. Vapor removal from the drying chamber can be accelerated by a small leak of an inert gas, preferably nitrogen.

Drying equipment preferably contains a stirrer, which is suitable to break the solid, forming a powder. After breaking the solid, API drying can be continued under reduced pressure, preferably with stirring until the residual solvent concentration reduces to the required FDA level. The solvent level depends on the type of solvent, but is preferably no more than about 5000 ppm, more preferably no more than about 4000 ppm, and most preferably no more than about 3000 ppm. The drying of the powder after the stirring is preferably carried out under reduced pressure (below 1 atm), more preferably below about 100 mm Hg, most preferably below about 50 mm Hg. The temperature is preferably about 30° C. to about 50° C., more preferably about 35° C. to about 45° C. The drying is preferably carried out for about 1 hour to about 10 hours.

The powder may be discharged from the dryer by any conventional means known to the skilled artisan, for example via an outlet located at the bottom of the chamber, while the stirrer is rotating. A valve may be opened to discharge the powder, and pressure may be applied to accelerate the discharge.

The process of the present invention is preferably carried out with a feeding system having the following properties: a distributor of preferably less than about 3 mm diameter syringe/nozzle, more preferably less than about 2 mm; continuous feeding of API solution, where the solution is in organic or aqueous solvent; working pressure of preferably less than about 760 mm Hg, more preferably less than about 100 mm Hg, more preferably less than about 50 mm Hg, most preferably less than about 20 mm Hg; working temperature of less than about 100° C., preferably about 20° C. to about 80° C., more preferably about 25° C. to about 45° C.; optional inert gas flow (such as $N_2$); and a drying chamber with stirrer and a discharge device. While dropwise addition is possible, scaling up the process for use on an industrial scale is easier with a syringe and continuous feeding.

By way of non-limiting example, 15 g cinacalcet HCl would preferably require the following parameters: 4 hours, 60±5° C., and 80 mm Hg. The solution is fed into the dryer at ambient temperature and amorphous cinacalcet HCl is obtained.

In another embodiment, the present invention encompasses pharmaceutical compositions comprising amorphous cinacalcet HCl, wherein the formulation is substantially stable against physical and chemical transformation, or the formulation is manufactured in accordance with acceptable Good Manufacturing Process ("GMP") requirements.

The following non-limiting examples are merely illustrative of the preferred embodiments of the present invention, and are not to be construed as limiting the invention, the scope of which is defined by the appended claims.

EXAMPLES

Instrumentation

Thermal Analysis

DSC analysis was performed using a Mettler Toledo 821 Star$^e$. The crucible was crimped and punched prior to analysis. The weight of the samples was about 3-5 mg; the samples were scanned at a rate of 10° C./min from 30° C. to 250° C. The oven was constantly purged with nitrogen gas at a flow rate of 40 mL/min. Standard 40 µl aluminum crucibles covered by lids with 3 holes were used.

Thermal weight change measurements were made on a Mettler TG50 Thermogravimetric Analyzer. Samples of 7-15 mg were placed in an aluminum pan and placed in the device. The data was collected from about 50° C. to about 350° C. at a rate of 10° C./min.

PXRD

Powder X-Ray powder diffraction data were obtained using a SCINTAG powder X-Ray diffractometer model X'TRA equipped with a solid state detector and a variable gonimeter. Copper radiation of 1.5418 Å was used. A round standard aluminum sample holder with round zero background, and cavity of 25(diameter)*0.5(dept) mm. Scanning parameters were in the range of 2-40°2θ and a continuous scan rate of 3°/min.

Equipment for Spray Drying

Manufacturer: Hosokawa Micron Corporation; Model: AGM-2M-SD

Stability of Amorphous Cinacalcet HCl

Example 1

Amorphous Cinacalcet HCl was stored at ambient temperature in a closed bottle for 2 months. The sample was tested by PXRD, showing amorphous content.

Water Content of Amorphous Cinacalcet HCl after Exposure to Humidity

Example 2

100 mg amorphous cinacalcet HCl was spread as a thin layer, and exposed to 100 percent relative humidity for 8 days. The sample was than tested by PXRD and by Karl Fischer ("KF") titration. Amorphous cinacalcet HCl was obtained with water content of 1.4 percent.

Preparation of Cinacalcet Base

Example 3

25.5 g of mesylate (VI) were dissolved in acetonitrile (204 ml). (R)-1-Naphtylethyl amine (14.5 ml) and anhydrous $K_2CO_3$ (24.9 g) were added and the reaction mixture was heated to reflux temperature and maintained at reflux for 16 hours. Then salts were filtered out and the solvent was removed under reduced pressure. The residue was dissolved in DCM (75 ml). The obtained solution was washed with 5 percent aqueous HCl solution (pH=1), followed by a saturated solution of $NaHCO_3$ (pH=8-9), and finally with water. The organic phase was then separated and dried over $Na_2SO_4$ (which is optional) and filtered. The solvent was evaporated until dryness to obtain 33.4 g of cinacalcet base.

Preparation of Amorphous Cinacalcet HCl—Solvent-Anti-solvent Method

Example 4

0.52 g of cinacalcet HCl was dissolved in chloroform (3.5 ml) at room temperature. Then n-pentane (30 ml) was added in one portion to obtain a precipitate. The slurry was stirred at room temperature for 5 minutes. The solid was then isolated by filtration and dried at 50° C. in a vacuum oven for 16 hours to obtain amorphous cinacalcet HCl.

Example 5

0.58 g of cinacalcet HCl was dissolved in chloroform (6 ml) at room temperature. Then n-heptane (30 ml) was added in one portion to obtain a precipitate. The slurry was stirred at room temperature for 16 hours. The solid was then isolated by filtration and dried at 50° C. in a vacuum oven for 20.5 hours to obtain amorphous cinacalcet HCl.

Example 6

0.62 g of cinacalcet HCl was dissolved in chloroform (4 ml) at room temperature. Then n-hexane (30 ml) was added in one portion to obtain a precipitate. The slurry was stirred at room temperature for 16 hours. The solid was then isolated by filtration and dried at 50° C. in a vacuum oven for 24.5 hours to obtain amorphous cinacalcet HCl.

Example 7

0.47 g of cinacalcet HCl was dissolved in chloroform (3.5 ml) at room temperature. Then cyclohexane (30 ml) was added in one portion to obtain a precipitate. The slurry was stirred at room temperature for 16 hours. The solid was then isolated by filtration and dried at 50° C. in a vacuum oven for 18.5 hours to obtain amorphous cinacalcet HCl.

Example 8

0.49 g of cinacalcet HCl was dissolved in chloroform (5 ml) at room temperature. Then cyclohexane (30 ml) was added in one portion to obtain a precipitate. The slurry was stirred at room temperature for 3 minutes. The solid was then isolated by filtration and dried at 50° C. in a vacuum oven for 24 hours to obtain amorphous cinacalcet HCl.

Preparation of Amorphous Cinacalcet HCl by Spray Dryer

Example 9

5.0 g cinacalcet HCl was dissolved in 95 percent ethanol (25 ml) at room temperature. The solution was spray dried using a Buchi mini spray dryer B-290 using a standard nozzle, 0.7 mm in diameter, with a nozzle cap of 1.4 mm. Nitrogen gas was at an inlet temperature of 100° C. The evaporated solvent and nitrogen left the spray dryer at a temperature of 65-60° C. Amorphous cinacalcet HCl was obtained.

Preparation of Amorphous Cinacalcet HCl by Rapid Vacuum Evaporation

Example 10

15 g of cinacalcet HCl is dissolved in 95 percent Ethanol (75 ml) at room temperature. The solution is fed into a pre-heated (60° C.) 1 L reactor under vacuum (~80 mbar) to obtain amorphous Cinacalcet HCl. Drying is carried out for about 4 hours. Amorphous Cinacalcet HCl is obtained.

Having thus described the invention with reference to particular preferred embodiments and illustrative examples, those in the art would appreciate modifications to the invention as described and illustrated that do not depart from the spirit and scope of the invention as disclosed in the specification. The examples are set forth to aid in understanding the invention, but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety.

What is claimed is:

1. Amorphous cinacalcet hydrochloride.
2. The amorphous Cinacalcet hydrochloride of claim 1, characterized by an X-ray diffraction pattern, substantially as depicted in FIG. 2.
3. A process for preparing the amorphous Cinacalcet HCl, the process comprising dissolving Cinacalcet HCl in chloroform; admixing an anti solvent selected from the group consisting of aliphatic and cyclic hydrocarbons to obtain a precipitate; and drying precipitated Cinacalcet hydrochloride under reduced pressure at temperature greater than 2520 C.
4. The process of claim 3, wherein amorphous Cinacalcet HCl is in a concentration of about 5 to about 10 ml of chloroform per gram of Cinacalcet hydrochloride.
5. The process of claim 3, wherein the anti-solvent is n-pentane, n-hexane, n-heptane, or cyclohexane.
6. The process of claim 3, wherein, subsequent to admixing the anti-solvent, the precipitate is maintained as a slurry for about 5 minutes to about 20 hours.
7. The process of claim 3, wherein the temperature is from about 40° C. to 60° C.
8. The process of claim 7, wherein the temperature is about 50° C.
9. The process of claim 3, wherein the precipitated Cinacalcet hydrochloride is dried for about 16 to 30 hours.
10. A process for preparing the amorphous Cinacalcet hydrochloride, comprising providing a solution of Cinacalcet hydrochloride in a solvent selected from the group consisting of a $C_2$ to $C_8$ ether, a $C_{5-8}$ cyclic, branched and/or halogenated hydrocarbon, a $C_{3-7}$ ester, a $C_{1-4}$ alcohols, a $C_{3-6}$ ketone, and mixtures thereof, and evaporating and removing the solvent by spray drying with nitrogen gas, having an inlet temperature of about 50° C. to 200° C.

11. The process of claim 10, wherein the solvent is selected from the group consisting of ethanol, THF, 1,4-Dioxane, dichloromethane, chloroform, ethylacetate, isobutyl acetate, acetone, MEK, and acetonitrile.

12. The process of claim 11, wherein the solvent is ethanol.

13. The process of claim 10, wherein the Cinacalcet hydrochloride is at a concentration of about 5 to about 10 ml of solvent per gram of Cinacalcet hydrochloride.

14. The process of claim 10, wherein the evaporated solvent and nitrogen exit the spray dryer at a temperature of about 25° C. to about 150° C.

15. A process for preparing the amorphous Cinacalcet hydrochloride, comprising providing a solution of Cinacalcet hydrochloride in a solvent, and removing the solvent by rapid vacuum evaporation under a pressure of less than about 760 mm Hg and a temperature of less than about 100° C.

16. The process of claim 15, wherein the pressure is less than about 100 mm Hg.

17. The process of claim 16, whereinthe pressure is less than about 70 mm Hg.

18. The process of claim 15, wherein the temperature is about 20° C. to about 80° C.

19. The process of claim 18, wherein the temperature is about 25° C. to about 45° C.

20. The process of claim 15, wherein the concentration and solvent of the solution, and the temperature, vacuum and feeding rate of the rapid vacuum evaporation are such that the Cinacalcet hydrochloride precipitates substantially instantly.

21. The process of claim 15, wherein the solvent is selected from the group consisting of a $C_{1-4}$ alcohol, a $C_{3-7}$ ketone, a $C_{3-7}$ ester, a $C_{5-7}$ linear, branched or cyclic, saturated or unsaturated hydrocarbon, a $C_2$ to $C_8$ ether, or mixtures thereof.

22. The process of claim 21, wherein the solvent is selected from the group consisting of methanol, ethanol, acetone, ethylacetate, heptane, hexane, diethylether methyl isobutylether, or mixtures thereof.

23. The process of claim 22, wherein the solvent is methanol or acetone.

24. The process of claim 21, wherein the solvent contains less than about 20% water by volume.

25. The process of claim 21, wherein the solvent contains less than about 10% water by volume.

26. The process of claim 21, wherein the solvent contains less than about 2% water by volume.

* * * * *

UNITED STATES PATENT AND TRADEMARK OFFICE
CERTIFICATE OF CORRECTION

PATENT NO. : 7,368,606 B2  Page 1 of 1
APPLICATION NO. : 11/439705
DATED : May 6, 2008
INVENTOR(S) : Lifshitz-Liron et al.

It is certified that error appears in the above-identified patent and that said Letters Patent is hereby corrected as shown below:

Column 8, line 47-48, change "2520C" to -- 25°C --

Signed and Sealed this

Second Day of June, 2009

JOHN DOLL
*Acting Director of the United States Patent and Trademark Office*